United States Patent
Adachi et al.

(10) Patent No.: US 8,340,241 B2
(45) Date of Patent: Dec. 25, 2012

(54) IMAGE DISPLAY APPARATUS AND X-RAY COMPUTED TOMOGRAPHY APPARATUS

(75) Inventors: Akira Adachi, Otawara (JP); Satoshi Saito, Yaita (JP)

(73) Assignees: Kabushiki Kaisha Toshiba, Tokyo (JP); Toshiba Medical Systems Corporation, Otawara-Shi (JP)

(*) Notice: Subject to any disclaimer, the term of this patent is extended or adjusted under 35 U.S.C. 154(b) by 0 days.

(21) Appl. No.: 11/678,730

(22) Filed: Feb. 26, 2007

(65) Prior Publication Data

US 2007/0201610 A1 Aug. 30, 2007

(30) Foreign Application Priority Data

Feb. 27, 2006 (JP) .............................. P2006-050825

(51) Int. Cl.
*A61B 6/00* (2006.01)
*G06K 9/00* (2006.01)
(52) U.S. Cl. .................... 378/4; 378/15; 382/131
(58) Field of Classification Search .............. 378/4, 15; 382/131, 132
See application file for complete search history.

(56) References Cited

U.S. PATENT DOCUMENTS

| | | | | |
|---|---|---|---|---|
| 4,550,371 A * | 10/1985 | Glover et al. | | 378/4 |
| 4,670,892 A * | 6/1987 | Abele et al. | | 378/4 |
| 4,991,092 A * | 2/1991 | Greensite | | 382/131 |
| 5,164,590 A * | 11/1992 | Coles et al. | | 250/255 |
| 5,170,347 A * | 12/1992 | Tuy et al. | | 345/419 |
| 5,268,967 A * | 12/1993 | Jang et al. | | 382/132 |
| 5,412,703 A * | 5/1995 | Goodenough et al. | | 378/8 |
| 5,430,291 A * | 7/1995 | Pepin et al. | | 250/255 |
| 5,490,221 A * | 2/1996 | Ransford et al. | | 382/130 |
| 5,640,436 A * | 6/1997 | Kawai et al. | | 378/4 |
| 5,859,891 A * | 1/1999 | Hibbard | | 378/62 |
| 5,960,056 A * | 9/1999 | Lai | | 378/4 |
| 6,014,419 A | 1/2000 | Hu | | |
| 6,028,909 A * | 2/2000 | Zmora | | 378/15 |
| 6,130,930 A | 10/2000 | Tam | | |
| 6,373,487 B1 * | 4/2002 | Culbertson et al. | | 345/424 |
| 6,408,042 B1 * | 6/2002 | Hsieh | | 378/4 |
| 6,415,048 B1 * | 7/2002 | Schneider | | 382/131 |
| 6,584,166 B2 | 6/2003 | Taguchi | | |
| 6,891,963 B1 | 5/2005 | Goto et al. | | |
| 6,925,141 B2 * | 8/2005 | Bruder et al. | | 378/8 |

(Continued)

FOREIGN PATENT DOCUMENTS

JP 2002-360562 12/2002

(Continued)

OTHER PUBLICATIONS

Feldkamp et al., Practical cone-beam algorithm, J. Opt Soc Am, vol. 1, No. 6, Jun. 1984, pp. 612-619.*

*Primary Examiner* — Alexander H Taningco
(74) *Attorney, Agent, or Firm* — Oblon, Spivak, McClelland, Maier & Neustadt, L.L.P.

(57) ABSTRACT

An X-ray computed tomography apparatus has an area arithmetic unit and an image processing unit. The area arithmetic unit obtains information with respect to a position of a deteriorating area appeared around an end on an acquisition range of a projection data under an influence of a cone angle. The image processing unit performs an image processing for a CT image to be discriminable the deteriorating area from an area other than the deteriorating area.

8 Claims, 11 Drawing Sheets

U.S. PATENT DOCUMENTS

| | | | |
|---|---|---|---|
| 6,990,169 B2 * | 1/2006 | Claus et al. | 378/4 |
| 7,277,567 B2 * | 10/2007 | Miyamoto et al. | 382/131 |
| 7,577,282 B2 * | 8/2009 | Gkanatsios et al. | 382/128 |
| 7,593,562 B2 * | 9/2009 | Harrington et al. | 382/141 |
| 7,747,056 B2 * | 6/2010 | Suzuki et al. | 382/131 |
| 2001/0031920 A1 * | 10/2001 | Kaufman et al. | 600/431 |
| 2002/0114530 A1 * | 8/2002 | Duarte | 382/254 |
| 2003/0031290 A1 * | 2/2003 | Sugihara et al. | 378/15 |
| 2003/0118226 A1 * | 6/2003 | Winsor et al. | 382/132 |
| 2003/0161434 A1 * | 8/2003 | Rand et al. | 378/4 |
| 2004/0066876 A1 | 4/2004 | Tam | |
| 2004/0066911 A1 * | 4/2004 | Hsieh et al. | 378/901 |
| 2004/0073584 A1 * | 4/2004 | Hsieh et al. | 708/200 |
| 2004/0174946 A1 * | 9/2004 | Hsieh | 378/4 |
| 2004/0264625 A1 * | 12/2004 | Basu et al. | 378/4 |
| 2005/0135550 A1 * | 6/2005 | Man et al. | 378/9 |
| 2005/0147198 A1 * | 7/2005 | Kiyono | 378/4 |
| 2005/0175144 A1 * | 8/2005 | Hsieh | 378/19 |
| 2006/0008049 A1 * | 1/2006 | Matsumoto | 378/19 |
| 2007/0140537 A1 * | 6/2007 | Heigl et al. | 382/128 |
| 2007/0237288 A1 * | 10/2007 | Tkaczyk et al. | 378/5 |

FOREIGN PATENT DOCUMENTS

| | | | |
|---|---|---|---|
| WO | WO 2005/078661 A1 | 8/2005 | |

* cited by examiner

IMAGE DISPLAY APPARATUS AND X-RAY COMPUTED TOMOGRAPHY APPARATUS

BACKGROUND OF THE INVENTION

1. Field of the Invention

The present invention relates to an image processing of a computed tomography (CT) image generated by using multi-arrayed detecting elements along a body axis, and especially to an image display apparatus and an X-ray CT apparatus for an image reconstruction processing using algorithm capable of reproducing a cone angle in the body axis direction faithfully and for clarifying a range that the image reconstruction processing is possible.

2. Description of the Related Art

In a generally employed X-ray CT apparatus, an X-ray tube and an X-ray detector with a plurality of segments (a plurality of arrayed detecting elements along a body axis direction (channel direction)) are oppositely placed to interpose an object, for example, a patient. The X-ray tube irradiates an X-ray beam to a predetermined site of the patient while rotating around the patient at "360°" together with the X-ray detector. The X-ray detector measures an X-ray dose that transmits the predetermined site of the patient as projection data. By the image reconstruction processing based on the projection data by using a computer, a CT image of the predetermined site is obtained.

There is a generally employed X-ray CT apparatus that has the X-ray detector with the segments from "2" to "64" on the body axis direction, known as "multi", now in the world. About the generally employed X-ray CT apparatus, there is the following characteristic. When an art used in the generally employed multi-X-ray CT apparatus is just applied to an X-ray CT apparatus having an X-ray detector with "64" or more segments, there is a following problem.

It depends on a length of the segments along the body axis direction, a distance between the X-ray tube and the object, a field of view (FOV), and a cone angle, but in a case where the X-ray detector with "64" or more segments on the body axis direction is used, two areas are expected to appear on the CT image, that is, a deteriorating area caused by the relatively insufficient projection data due to the cone angle of the X-ray, and a non-deteriorating area with relatively sufficient projection data. However, when only the non-deteriorating area tends to appear on the CT image by using the generally employed multi-X-ray CT having the X-ray detector with the segments from "2" to "64", the deteriorating area appeared on the CT image was rarely distinguished on displaying.

In a case where the deteriorating area on the CT image is intended to be masked, an operator is unable to identify a range to be masked upon CT inspection, and accordingly, fails to determine whether or not the required scan area covers the predetermined site of the patient before a scan.

SUMMARY OF THE INVENTION

The present invention has taken into consideration the above-described problems, and it is an object of the present invention to provide the image display apparatus and the X-ray CT apparatus, an image that can effectively perform an inspection and an interpretation of radiogram is offered.

To solve the above-described problems, the present invention provides the image display apparatus that acquires projection data while rotating an X-ray source for emitting an X-ray beam and an X-ray detector including multi-arrayed detecting elements along a slice direction around a rotary axis, and displays a CT image that is reconstructed by performing a back projection in consideration with a cone angle of the X-ray beam, comprising: an area arithmetic unit configured to obtain information with respect to a position of a deteriorating area appeared around an end on an acquisition range of the projection data under an influence of the cone angle; and a display controlling processing unit configured to control a displaying of the CT image in a display format that be discriminable the deteriorating area from an area other than the deteriorating area, based on the information with respect to the position of the deteriorating area.

To solve the above-described problems, the present invention provides the X-ray computed tomography apparatus that acquires projection data while rotating an X-ray source for emitting an X-ray beam and an X-ray detector including multi-arrayed detecting elements along a slice direction around a rotary axis, and reconstructs a CT image by performing a back projection in consideration with a cone angle of the X-ray beam, comprising: an area arithmetic unit configured to obtain information with respect to a position of a deteriorating area appeared around an end on an acquisition range of the projection data under an influence of the cone angle; and an image processing unit configured to perform an image processing for the CT image to be discriminable the deteriorating area from an area other than the deteriorating area.

To solve the above-described problems, the present invention provides the X-ray computed tomography apparatus that acquires projection data while rotating an X-ray source for emitting an X-ray beam and an X-ray detector including multi-arrayed detecting elements along a slice direction around a rotary axis, and reconstructs a CT image by performing a back projection in consideration with a cone angle of the X-ray beam, comprising: a display device configured to display an image for a positioning of an object that is obtained by a scan for the object and an image of a mark indicating a scan range by superimposing, and to display the image of the mark on the image for the positioning so as to be discriminable the deteriorating area; and an input device configured to enable a signal input of the scan range to obtain the CT image.

To solve the above-described problems, the present invention provides the X-ray computed tomography apparatus that acquires projection data while rotating an X-ray source for emitting an X-ray beam and an X-ray detector including multi-arrayed detecting elements along a slice direction around a rotary axis, and reconstructs a CT image by performing a back projection in consideration with a cone angle of the X-ray beam, comprising: an image processing unit configured to perform at least any one of operations to hide a display, to change a color, and to lower a contrast with respect to the deteriorating area on a scanogram for a positioning of an object that is obtained by a scan for the object; a display device configured to display the scanogram generated by the image processing unit, and an image of a mark indicating a scan range by superimposing; and an input device configured to enable a signal input of the scan range to obtain the CT image.

To solve the above-described problems, the present invention provides the X-ray computed tomography apparatus that acquires projection data while rotating an X-ray source for emitting an X-ray beam and an X-ray detector including multi-arrayed detecting elements along a slice direction around a rotary axis, and reconstructs a CT image by performing a back projection in consideration with a cone angle of the X-ray beam, comprising: an area arithmetic unit configured to obtain information with respect to a position of a deteriorating area appeared around an end on an acquisition range of the projection data under an influence of the cone angle; and an image processing unit configured to perform an image processing for the CT image so as to be discriminable the deteriorating area.

DESCRIPTION OF THE PREFERRED EMBODIMENTS

An embodiment of an image display apparatus and an X-ray CT apparatus according to the present invention will be described referring to the accompanied drawings.

There are various types of the X-ray CT apparatus, for example, a type of "ROTATE/ROTATE" in which an X-ray tube and an X-ray detector are integrally rotated around an object, a type of "STATIONARY/ROTATE" in which a large number of detecting elements are ring-like arrayed such that only the X-ray tube is rotated around the object, and the like. The present embodiment is applicable to the X-ray CT apparatus of arbitrary type. In the embodiment, the explanation with respect to the X-ray CT apparatus of the type of "ROTATE/ROTATE" which has been used as the mainstream trend will be made hereinafter. In order to reconstruct a single slice of CT image data, projection data of full circle of the object at approximately "360°" are required. Alternatively, the projection data of half circle of the object at "180°" plus a view angle are required in case of a half scan method. The present embodiment is applicable to any one of the aforementioned reconstruction methods. As a mechanism for converting an incident X-ray into an electric charge, a type of indirect conversion and a type of direct conversion have been employed as the mainstream trend. In the type of indirect conversion, the incident X-ray is converted into a light by a fluorescent material such as a scintillator, and the light is converted into the electric charge using a photoelectric conversion element such as a photodiode. Meanwhile, the type of direct conversion of the incident X-ray is performed by forming an electron-hole pair within a semiconductor so as to be conducted to an electrode, that is, using a photoconductive effect of the X-ray. An arbitrary type of the aforementioned X-ray detector element may be employed. Recently, an X-ray CT apparatus with so-called multi-X-ray tube has been increasingly produced and the peripheral techniques have also been developed. In the X-ray CT apparatus with so-called multi-X-ray tube, plural pairs of the X-ray tube and the X-ray detector are installed in a rotary frame. The present embodiment is applicable to either the generally employed the X-ray CT apparatus with the single tube or the X-ray CT apparatus with so-called multi-X-ray tube. In the embodiment, the X-ray CT apparatus with the single tube will be described hereinafter.

Figure 1:
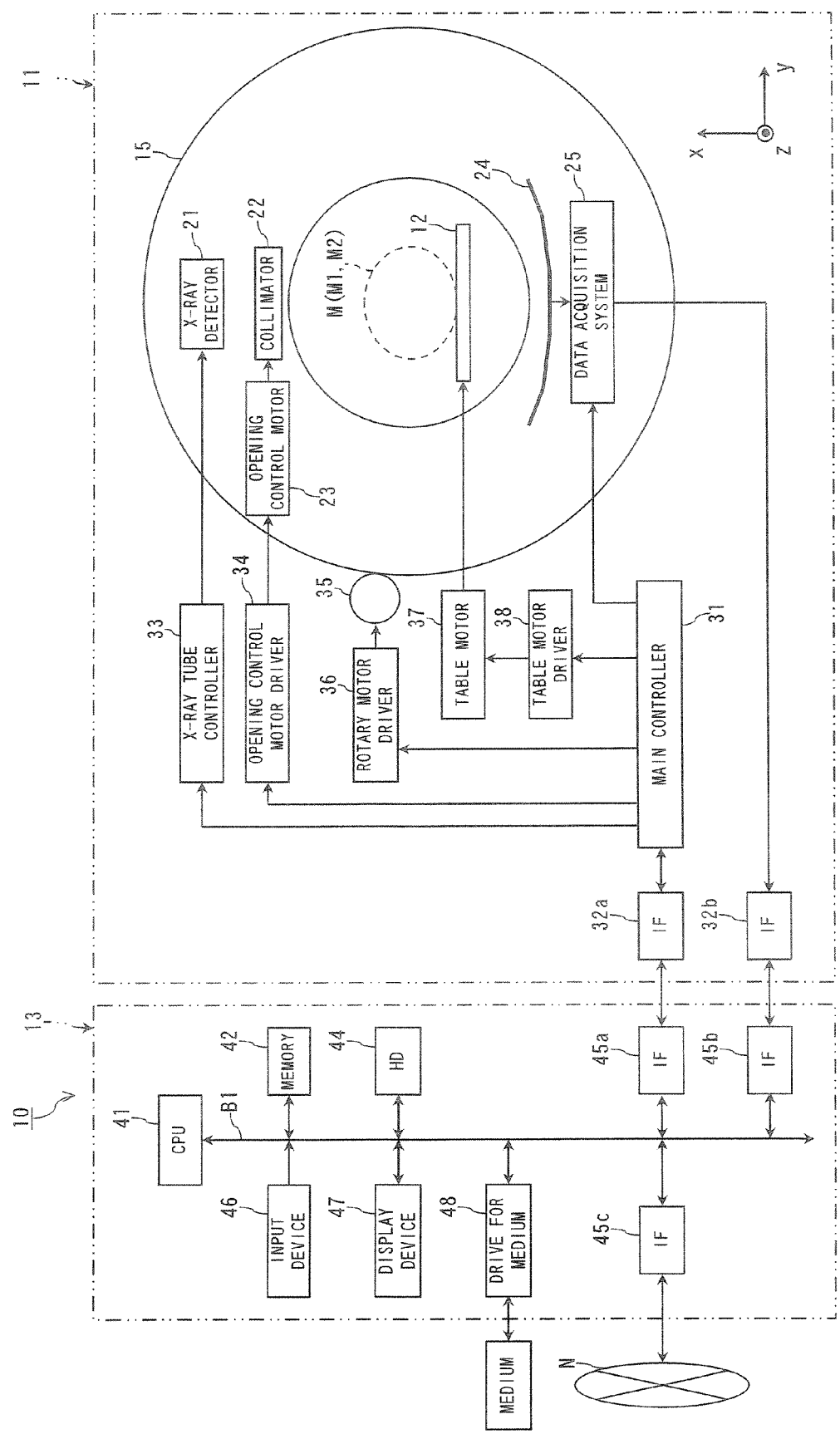
FIG. 1 is a block diagram of an embodiment of an X-ray CT apparatus according to the present invention.

FIG. 1 is a block diagram of an embodiment of an X-ray CT apparatus according to the present invention.

FIG. 1 shows an X-ray CT apparatus 10 which acquires projection data while rotating the X-ray source that irradiates an X-ray beam and the X-ray detector including a plurality of arrayed detecting elements along a z-axis direction (body axis direction, slice direction) around a rotary axis, and reconstructs the CT image at each slice by performing a back projection in consideration with an cone angle of the X-ray beam. The X-ray CT apparatus 10 has a gantry 11 on which an object M (patient M1 or cylinder M2) is executed a scan with the X-ray, a table 12 that conveys the object M through the cavity of the gantry 11 in the z-axis direction, and an operation console 13 which controls the operation of the gantry 11 and reconstructs the CT image (axial image) based on the data transmitted from the gantry 11 so as to be output (displayed).

The gantry 11 operable in a tilt direction (not shown) has a rotary unit 15 and a fixed unit (not shown). The rotary unit 15 of the gantry 11 has an X-ray tube 21, a collimator 22, an opening control motor 23, an X-ray detector 24, and a data acquisition system (DAS) 25. The X-ray tube 21 and the collimator 22 are placed opposite the X-ray detector 24 such that the cavity of the gantry 11, that is, the object M is interposed therebetween. The rotary unit 15 is structured to rotate around the cavity while keeping the aforementioned positional relationship.

The fixed unit has a main controller 31, interfaces (IFs) 32a and 32b, an X-ray tube controller 33, an opening control motor driver 34, a rotary motor 35, a rotary motor driver 36, a table motor 37 and a table motor driver 38.

The driving operation of the X-ray tube 21 as the X-ray source is controlled by the X-ray tube controller 33 such that the X-ray is irradiated from a tube (not shown) of the X-ray tube 21 to the X-ray detector 24.

The driving operation of the collimator 22, having an opening for controlling the irradiation range of the X-ray from the X-ray tube 21, is controlled by the opening control motor driver 34.

The X-ray detector 24 has a plurality of segments (a plurality of the arrayed X-ray detecting elements along the z-axis direction (channel direction)) that detect the X-ray irradiated from the X-ray tube 21 via the collimator 22 and the cavity. In the z-axis direction of the X-ray detector 24, "64" or more segments of the X-ray detecting elements, for example, "256" segments are arranged in parallel with one another.

The data acquisition system 25 acquires signals output from the respective detection channels of the X-ray detector 24 as the projection data.

The main controller 31 analyzes respective commands received from the operation console 13 via the IF 32a, based on which various control signals are output to the X-ray tube controller 33, the opening control motor driver 34, the rotary motor driver 36, the table motor driver 38 and the data acquisition system 25, respectively.

The X-ray tube controller 33 transmits a drive signal to the X-ray tube 21 so as to generate the X-ray.

The opening control motor driver 34 transmits a drive signal to the opening control motor 23 so as to adjust the aperture of the collimator 22.

The rotary motor driver 36 transmits a drive signal to the rotary motor 35 so as to rotate the rotary unit 15 around the cavity while keeping its positional relationship.

The table motor driver 38 transmits a drive signal to the table motor 37 so as to convey the table 12 in the z-axis direction.

The projection data acquired by the data acquisition system 25 are transmitted to the operation console 13 via the IF 32b.

The operation console 13 is structured based on a computer as so-called workstation and may be bilaterally communicated with the network N, for example, local area network (LAN) constructed in the hospital. The operation console 13 is mainly formed of a basic hardware including a central processing unit (CPU) 41, a memory 42, a hard disc (HD) 44, IFs 45a, 45b and 45c, an input device 46 and a display device 47. The CPU 41 is interconnected with the respective units of the hardware that forms the operation console 13 via a bus B1 as the common signal transmission path. A drive for medium 48 may be added to the operation console 13.

The CPU 41 executes a program stored in the memory 42 in response to an instruction input through the operation of the input device 46 by an operator. Alternatively, the CPU 41 executes the program stored in the HD 44, the program transferred from the network N to the IF 45c to be installed in the HD 44, or the program read from the recording medium set in the drive for medium 48 through loading to the memory 42.

The memory 42 serves as a read only memory (ROA) and a random access memory (RAM) to store an initial program loading (IPL), a basic input/output system (BIOS) and the data as a storage device. The memory 42 may be a work memory of the CPU 41, and temporarily store the data.

The HD 44 is formed of a non-volatile semiconductor disk serving as the storage device, and stores the program installed in the operation console 13 (including operating system (OS) in addition to an application program) and the data. The OS may be structured to supply a graphical user interface (GUI) that allows the input device 46 to perform the basic operation for a graphics-laden display of the information for an operator.

The IFs 45a, 45b and 45c control the communication in accordance with the respective standards. The IFs 45a and 45b for communicating with the gantry 11 are connected to the IFs 32a and 32b of the gantry 11, respectively. The IF 45c has a function to connectable to the network N via a telephone line and so on. Accordingly, the operation consol 13 is connected from the IF 45c to the network N.

A keyboard and a mouse operable by the operator may be employed as the input device 46 such that a signal input in accordance with an operation is transmitted to the CPU 41. The operator is allowed to input a width of X-ray irradiated area (described later) in the z-axis direction to the operation console 13 via the input device 46. The operator is allowed to set a scan range (described later) for obtaining the CT image by the input operation via the input device 46.

A monitor may be employed as the display device 47. The CT image may be displayed on the display device 47 by developing the image data in a memory, for example, a video random access memory (VRAM) (not shown) that develops the image data intended to be displayed.

The drive for medium 48 allows the medium to be detachably set such that the data (including the program) stored in the medium are read to be output onto the bus B1. The data supplied through the bus B1 are written in the medium. The aforementioned medium may be supplied as a so-called package software.

Figure 2:
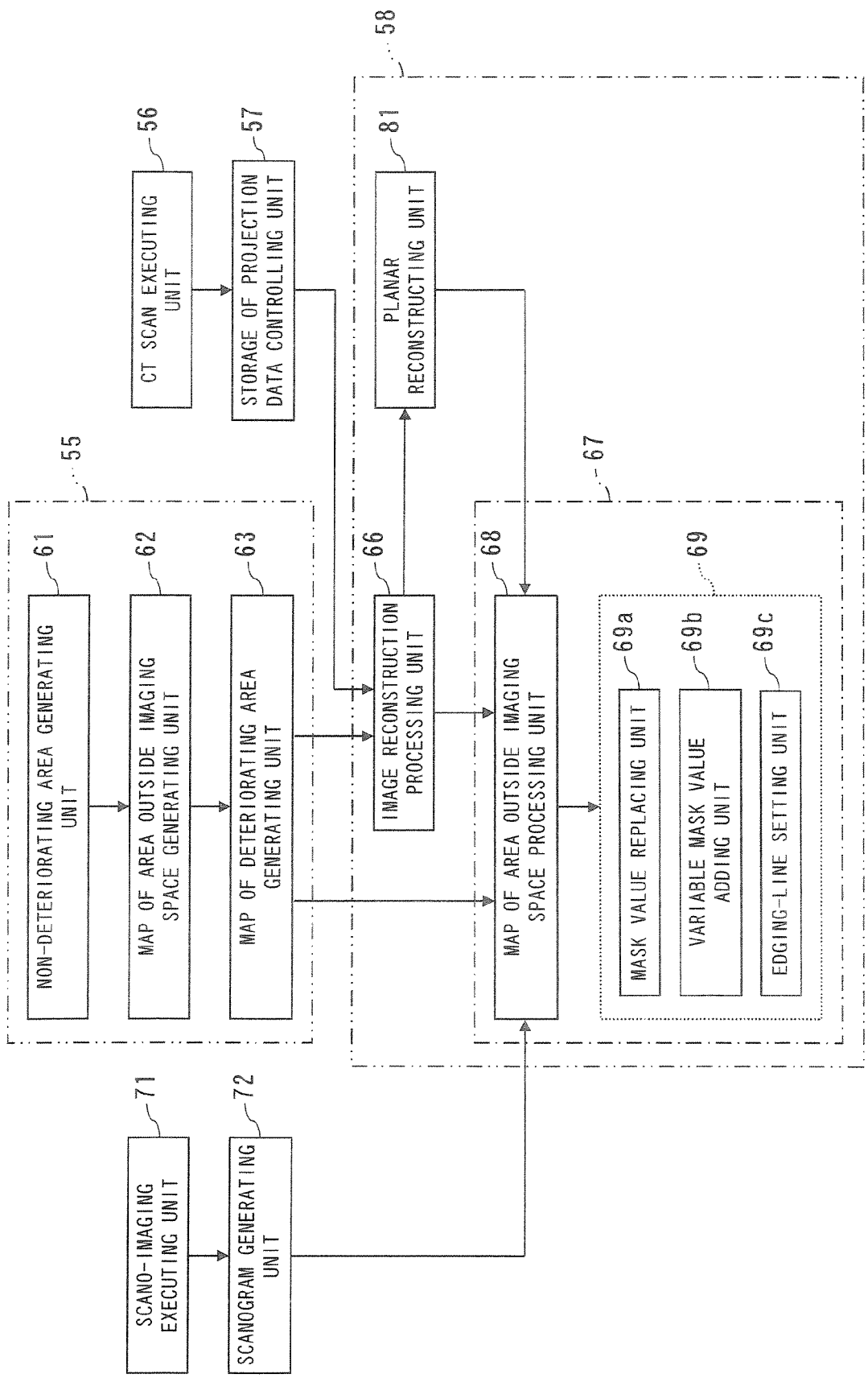
FIG. 2 is a functional block diagram of an operation console in the embodiment of the X-ray CT apparatus.

FIG. 2 is a functional block diagram of the operation console 13.

The operation console 13 (shown in FIG. 1) serves as an area arithmetic unit 55, a CT scan executing unit 56, a storage of projection data controlling unit 57 and an image processing unit 58 upon execution of the program by the CPU 41 of the operation console 13. The respective units from 55 to 58 are structured to be operated by executing the program. However, they are not limited to the structure as described above. Whole or part of the respective units from 55 to 58 may be formed as the hardware provided in the operation console 13.

The area arithmetic unit 55 has a function to obtain information with respect to a position of a deteriorating area (low quality area in the image data) generated around the end on an acquisition range of the projection data caused by the relative insufficiency of the projection data under an influence of the cone angle, a noise, and an image distortion based on a planar slice. More specifically, the area arithmetic unit 55 obtains the information with respect to an area outside an diameter of an imaging space, the position of the deteriorating area which appears around an end of the projection data acquisition range under the influence of the cone angle, and a position of a non-deteriorating area (normal quality area in the image data) other than the deteriorating area with relatively sufficient projection data, respectively based on the position information in the slice direction. The area arithmetic unit 55 has a non-deteriorating area generating unit 61, a map of area outside imaging space generating unit 62, and a map of deteriorating area generating unit 63.

In the present embodiment, when the X-ray irradiation at each projection angle (view angle) is executed for an area formed by the imaging space and a distance (VDS, described later) of the z-axis direction, there is a case that there are both with projection data obtained at a certain projection angle and projection data obtained at an opposed projection angle (around "180" degrees) of the certain projection angle. In this case, a data area of the projection data obtained at the certain projection angle and a data area of the projection data obtained at the opposed projection angle are compared. And, an area that reconstructed a data area where the data area of the projection data obtained at the certain projection angle and the data area of the projection data obtained at the opposed projection angle are not crossover is defined as the "deteriorating area".

The non-deteriorating area generating unit 61 has a function to generate the non-deteriorating area, appeared on the image data at each planar slice to assume a center of the rotary axis of the rotary unit 15 a center, based on the diameter of the imaging space, the width of the X-ray detector 24 in the z-axis direction, a distance between the x-ray tube 21 and the X-ray detector 24, and a diameter of the non-deteriorating area on the planar slice at a distal end.

Figure 3:
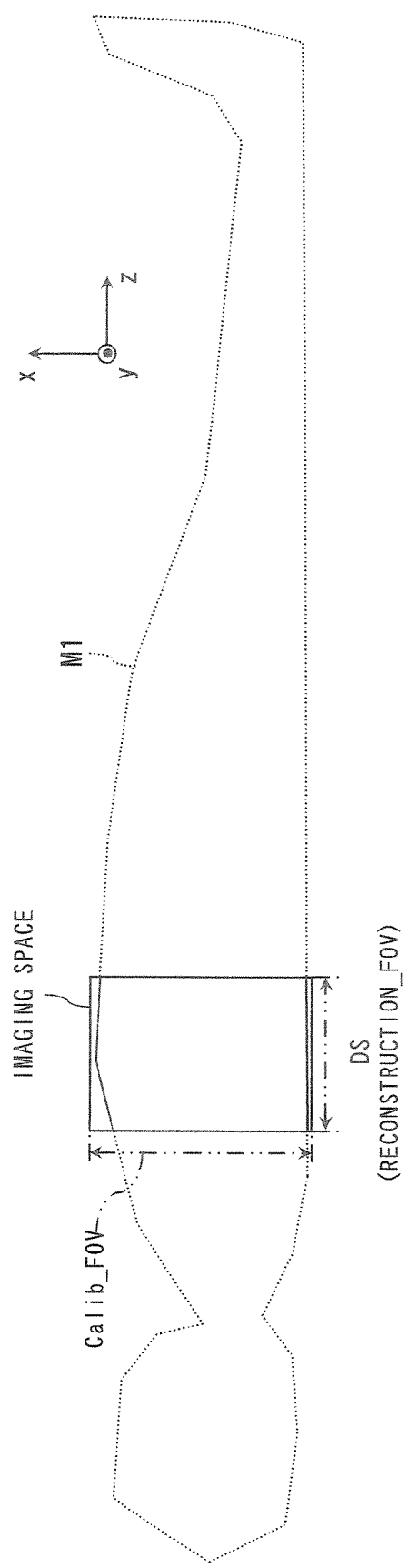
FIG. 3 is a diagram of a planar sagittal showing an imaging space at a predetermined site of a patient.

FIG. 3 is a diagram of a planar sagittal showing the imaging space at a predetermined site of the patient M1.

An x-axis direction of the imaging space (shown in FIG. 3) is determined by the number of the cylindrical models containing reference material, for example, a water phantom, and the arrangement thereof, and represents the diameter (Calibration_Field_Of_View: Calib_FOV) of the cylindrical imaging space at the axial center in the z-axis direction. Meanwhile, the z-axis direction represents a width (Detector_Size: DS) of the X-ray irradiated area in the z-axis direction of the X-ray detector 24, or a range (reconstruction_FOV) of the planar slice that can be reconstructed. As the "Calib_FOV" is determined by a diameter of a cylinder having the z-axis as an axial center, it may be kept constant by changing the z-axis direction.

The non-deteriorating area generating unit 61 has a function to generate a size (diameter) (Mask_FOV: M_FOV) of the deteriorating area to occur on each planar slice in the "reconstruction_FOV" at the rotary axis of the rotary unit 15 as the center, based on the "Calib_FOV", the "DS", the distance (focus center distance: FCD) between the X-ray tube 21 and the X-ray detector 24, and a size (diameter) of the non-deteriorating area on the planar slice (distal end of the reconstruction_FOV) at the distal end in the z-axis direction of the X-ray detector 24 at the rotary axis of the rotary unit 15 as the center, that is, a "Minimum_Mask_FOV (MM_FOV)". Farther, the "MM_FOV" may be input by the operator through the input device 46, or preliminarily set. In addition, the "MM_FOV" preliminarily set by the independent operator or the inspection site may be used.

Figure 4:
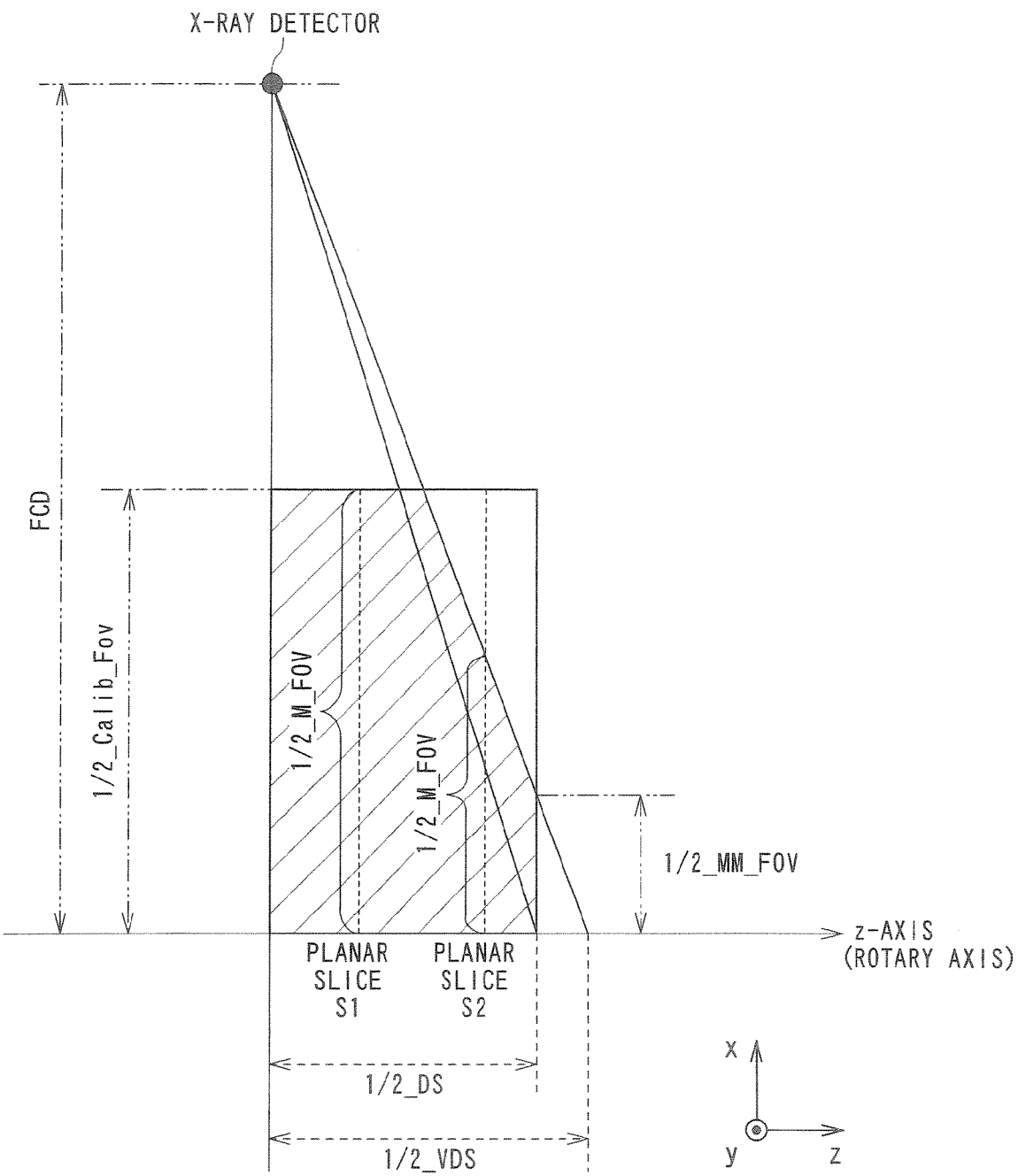
FIG. 4 is a diagram to explain how an "M_FOV" is generated.

FIG. 4 is a diagram to explain how the "M_FOV" is generated. FIG. 4 only shows the plane of a first quadrant of the x-z coordinate system (planar sagittal system) with a gravity center of the imaging space as the base point. In FIG. 4, the "Calib_FOV" is expressed as a radius, that is, a "½_Calib_FOV", the "DS" is expressed as a "½_DS", the "MM_FOV" is expressed as a radius, that is, a "½_MM_FOV". Referring to FIG. 4, the portion on the planar sagittal appeared as the non-deteriorating area on each planar slice at the rotary axis of the rotary unit 15 as the center is hatched.

For example, the operator inputs the "MM_FOV" into the operation console 13 through the input device 46 (shown in FIG. 1) so as to calculate the virtual width (Virtual_Detector_Size: VDS) of the X-ray detector 24 in the z-axis direction using the "MM_FOV", the "FCD", and the "DS" with a following Equation (1). In addition, according to FIG. 4, the "VDS" is expressed with a "½_VDS".

$$VDS = \frac{2 \times FCD \times DS}{FCD - MM\_FOV} \quad (1)$$

In addition, a coordinate (Dist) of the z-axis direction at a predefined planar slice is operated based on a size (SegSize) of the detecting elements of the X-ray detector 15, and a absolute value of a difference a segment number (Cseg) of the detecting element had at a center of the z-axis direction of the X-ray detector 24 and detecting element number (seg) at the predefined planar slice by a following Equation (2).

$$\text{Dist} = abs(C\text{seg} - \text{seg}) \times \text{SegSize} \quad (2)$$

Therefore, a provisional "M_FOV" (tmpM_FOV) at the predefined planar slice is obtained by a following Equation (3). That is to say, the "tmpM_FOV" changes at each planar slice.

$$\text{tmpM\_FOV} = \left(1 - \frac{Dist}{VDS}\right) \times 2 \times FCD \quad (3)$$

In addition, at the each planar slice, a small one is obtained as the "M_FOV", based on the "Calib_FOV" and the "tmpM_FOV" by a following Equation (4).

$$M\_FOV = \min(tmpM\_FOV, Calib\_FOV) \quad (4)$$

For example, in a case of a planar slice S1 during FIG. 4, the "M_FOV" seems to become a following Equation (5).

$$M\_FOV = Calib\_FOV \quad (5)$$

At the same time, in a case of a planar slice S2 during FIG. 4, the "M_FOV" seems to become a following Equation (6).

$$M\_FOV = tmpM\_FOV \quad (6)$$

The map of area outside imaging space generating unit 62 (shown in FIG. 2) has a function to generate a map of area outside imaging space which is an area outside the imaging space on each planar slice around a reconstruction center, using a generally employed process based on the "Calib_FOV" and the "reconstruction_FOV".

The map of deteriorating area generating unit 63 has a function to generate a map of deteriorating area of the deteriorating area appeared on each planar slice around a reconstruction center, based on the "Calib_FOV", the "reconstruction_FOV", and the "M_FOV" generated by the non-deteriorating area generating unit 61. The diameter (rate) of the deteriorating area may vary depending on the planar slice within the "reconstruction_FOV" as shown in FIG. 4.

Figure 5:
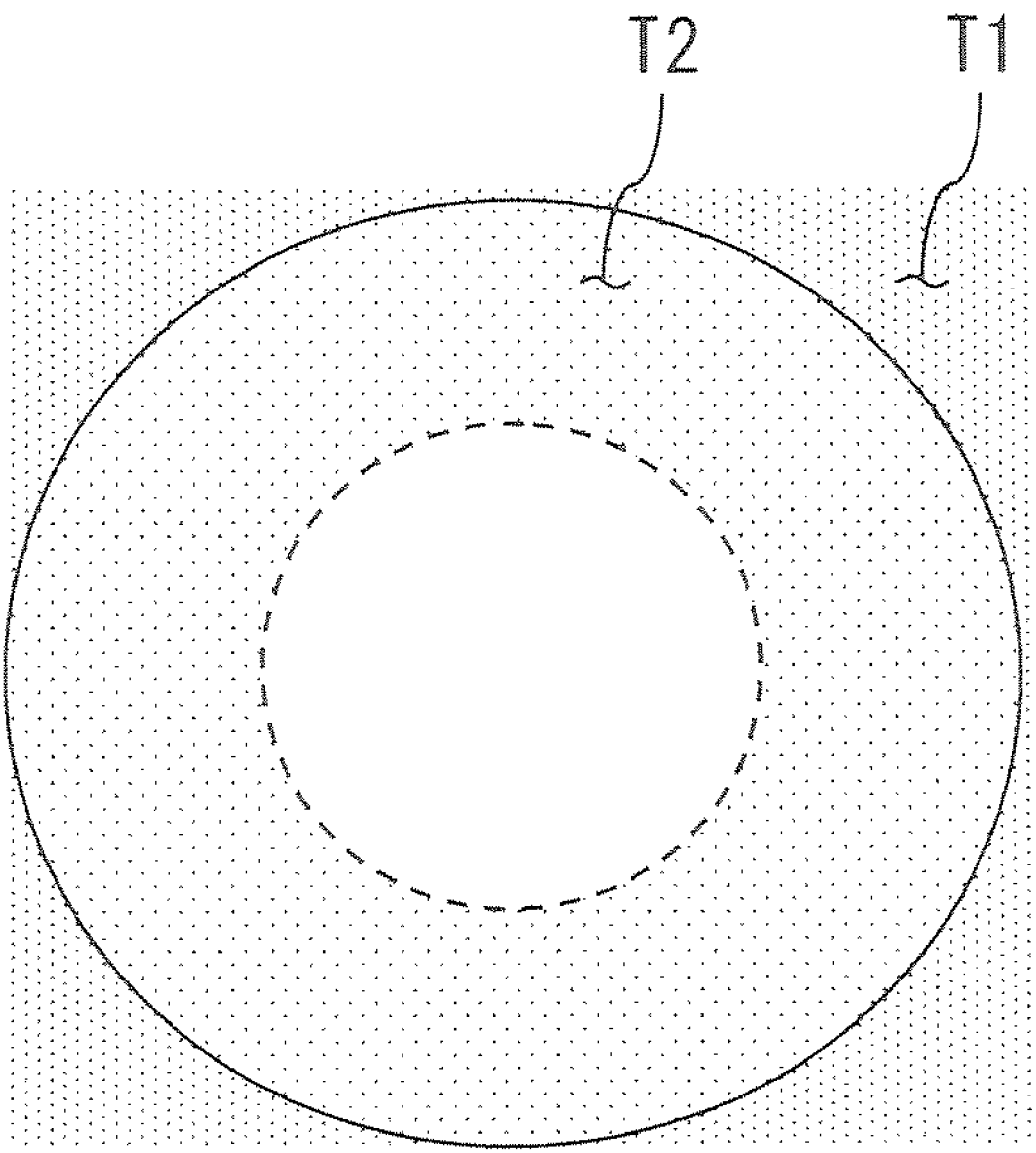
FIG. 5 is a diagram of an example showing a map of area outside imaging space and a map of deteriorating area on a planar CT.

FIG. 5 is a diagram of an example showing the map of area outside imaging space and the map of deteriorating area on the planar CT (planar axial).

FIG. 5 is a diagram of the planar slice S2 (shown in FIG. 4), and shows the map T1 of area outside imaging space and the map T2 of deteriorating area in the case where the rotary axis of the rotary unit 15 (shown in FIG. 1) coincides with the reconstruction center. The map T2 of deteriorating area is a doughnut-like map defined by a circular inner rim (dashed line in FIG. 5) and a circular outer rim (solid line in FIG. 5).

In a case where a tilt angle of the gantry 11 is "0°", the inner rim and the outer rim (inner rim of the map T1 of area outside imaging space) of the map T2 of deteriorating area are formed as circles as shown in FIG. 5. In a case where the tilt angle of the gantry 11 is the value other than "0°", they become oval. FIG. 5 shows the maps at the rotary axis of the rotary unit 15 that coincides with the reconstruction center. However, it is not limited to the one shown in the drawing. The rotary axis of the rotary unit 15 does not have to coincide with the reconstruction center. In such the case, the inner rim and the outer rim of the map T2 of deteriorating area may have an area that a part of is chipped off.

Furthermore, on the planar slice S1 (shown in FIG. 4), the map T2 of deteriorating area is not generated when the rotary axis of the rotary unit 15 (shown in FIG. 1) coincides with the reconstruction center.

The CT scan executing unit 56 (shown in FIG. 2) has a function to rotate the rotary unit 15 of the gantry 11 and to acquire the projection data by performing the CT scan. During the CT scan, the object M is positioned within the cavity of the rotary unit 15 for fixing the position in the z-axis direction, the X-ray beam from the X-ray tube 21 is irradiated to the object (X-ray projection), and a transmission X-ray is detected by the X-ray detector 24. The detection of the transmission X-ray is performed in N view directions (N=1000, for example) while rotating the X-ray tube 21 and the X-ray detector 24 around the object M at "360°" (changing the projection angle). The detected transmission X-ray is converted into the digital value by the data acquisition system 25, and transferred to the operation console 13 as the projection data via the IF 32b. The aforementioned series of the process may be referred to as a unit of "1" scan.

The storage of projection data controlling unit 57 has a function to control storage of the projection data transferred from the gantry 11 to the storage device, for example, the HD 44.

The image processing unit 58 has a function to reconstruct the CT image, to implement an image processing for the CT image such that the deteriorating area is discriminated from the non-deteriorating area, and to make the display device 47 display the processed image. The image processing unit 58 changes a feature of the image processing so as to be discriminable between the deteriorating area and the non-deteriorating area by performing the image processing for changing at least one of a gray-scale conversion feature and a tone feature on the CT image. The image processing unit 58 may perform the image processing to delete data corresponding to the deteriorating area from data of the CT image such that the deteriorating area is discriminated from the non-deteriorating area. Alternatively, the image processing unit 58 may perform at least any one of operations to hide the display, to change a color, and to lower a contrast with respect to the deteriorating area on the CT image such that the deteriorating area is discriminated from the non-deteriorating area. The image processing unit 58 may further be structured to display a boundary line to a circular inner rim of the deteriorating area (boundary between the deteriorating area and the non-deteriorating area) such that the deteriorating area is discriminated from the non-deteriorating area. More specifically, the image processing unit 58 has an image reconstruction processing unit 66 and a display controlling unit 67.

The image reconstruction processing unit 66 has a function to generate the CT image (reconstruction image) by back projecting the inside of the "Calib_FOV" (the deteriorating area and the non-deteriorating area) on each at the planar slice based on the projection data acquired by the CT scan executing unit 56 and stored in the storage of projection data controlling unit 57, or the projection data preliminarily stored in the storage device such as the HD 44. The image reconstruction process used for a conventional scan, a dynamic scan and a real time scan is performed using the algorithm that allows faithful reproduction of the cone angle in the z-axis direction.

The display controlling unit 67 has a function to control displaying of the image on the display device 47. Specifically, the display controlling unit 67 has a map of area outside imaging space processing unit 68 and a map of deteriorating area processing unit 69

The map of area outside imaging space processing unit 68 has a function to superimpose the map of area outside imaging space generated by the map of area outside imaging space generating unit 62 with the CT image reconstructed by the image reconstruction processing unit 66 in reference to the reconstruction center so as to convert a pixel value corresponding to the pixel within the map of area outside imaging space into the mask value (for example "−2048") that makes the image invisible.

The map of deteriorating area processing unit 69 has a function to convert a display format within the map of deteriorating area by superimposing the map of deteriorating area, generated by the map of deteriorating area generating unit 63, with the reconstructed CT image, generated by the image reconstruction processing unit 66, in reference to the reconstruction center. The map of deteriorating area processing unit 69 is provided with at least one of a mask value replacing unit 69a, a variable mask value adding unit 69b and an edging-line setting unit 69c.

The mask value replacing unit 69a replaces the pixel value corresponding to the pixel within the map of deteriorating area with the mask value that makes the image invisible.

The variable mask value adding unit 69b adds the variable mask value to the pixel value corresponding to the pixel within the map of deteriorating area for making a transparency of the mask within the map of deteriorating area variable.

The edging-line setting unit 69c serves to provide the rim of the map of deteriorating area with an edging-line.

Furthermore, by a size of a pixel of a reconstruction matrix (including a volume), there is a case that there is a pixel equivalent to both with the deteriorating area and the non-deteriorating area, in a vicinity of a border with a pixel falling under the deteriorating area on the map of deteriorating area and a pixel falling under the non-deteriorating area not on the map of deteriorating area and not on the map of area outside imaging space. In this case, for the pixel equivalent to both, the processing as the deteriorating area or the non-deteriorating area may be performed. Or, for the pixel equivalent to both, a processing, like gradation processing, of unlike the processing of the deteriorating area and the non-deteriorating area may be performed.

Figure 6:
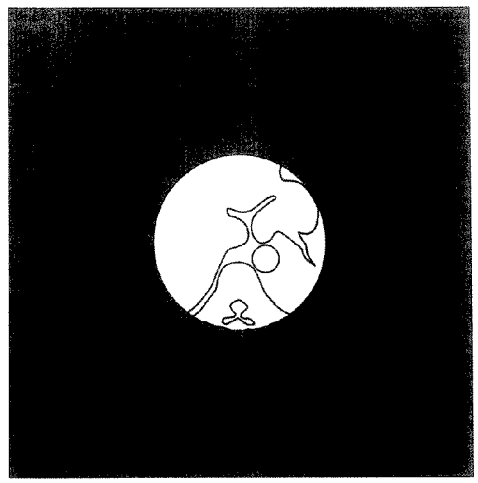
FIG. 6 is a pattern diagram showing an example of display method of an image including a CT image.
Figure 7:
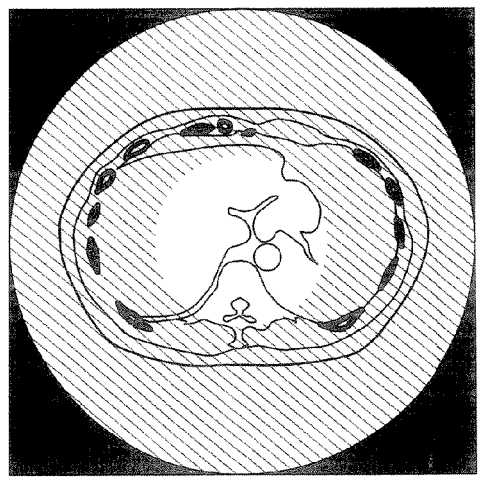
FIG. 7 is a pattern diagram showing an example of display method of the image including the CT image.
Figure 8:
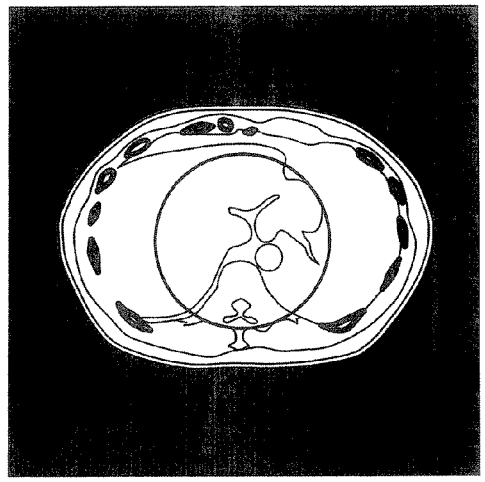
FIG. 8 is a pattern diagram showing an example of display method of the image including the CT image.

FIGS. 6, 7 and 8 are each pattern diagram showing an example of display method of the image including the CT image.

Each display image in FIGS. 6, 7 and 8 shows the planar slice S2 (shown in FIG. 4) representing the display image including the CT image in the case where the rotary axis of the rotary unit 15 coincides with the reconstruction center. FIG. 6 is the display image obtained by allowing the mask value replacing unit 69a of the map of deteriorating area processing unit 69 to function to replace the pixel value of the pixel within the map T2 of deteriorating area with the mask value. FIG. 7 is the display image obtained by allowing the variable mask value adding unit 69b of the map of deteriorating area processing unit 69 to function to add the variable mask value to the pixel value corresponding to the pixel within the map T2 of deteriorating area. The portion where the variable mask value is added to the pixel value is hatched. FIG. 8 is the display image obtained by allowing the edging-line setting unit 69c of the map of deteriorating area processing unit 69 to function to provide the inner rim of the map T2 of deteriorating area with the edging line (as solid circle in the drawing). In the case where the rotary axis of the rotary unit 15 does not coincide with the reconstruction center, the display image may have a missing portion.

In the present embodiment, the mask value replacing unit 69a of the map of deteriorating area processing unit 69 may be operated to discriminate the deteriorating area unsuitable for an inspection from the non-deteriorating area suitable for the inspection such that the pixel value within the map T2 of deteriorating area is replaced with the mask value likewise the map T1 of area outside imaging space, and the CT image that covers the non-deteriorating area is only displayed (see FIG. 6).

However, there may be a case where the replacement of the pixel values in the map T2 of deteriorating area with the mask value makes it difficult to identify as to which portion (site) of the patient M1 corresponds with the image within the deteriorating area, that is, difficult to determine the positional relationship to its entirety. In the present embodiment, the variable mask value adding unit 69b of the map of deteriorating area processing unit 69 is allowed to function to change the transparency of the mask applied to the map T2 of deteriorating area such that the positional relationship of the image within the deteriorating area to the entirety is identified for displaying the CT image that covers both the non-deteriorating area and the deteriorating area (see FIG. 7). Accordingly, this may indicate that the image within the map T2 of deteriorating area has the low quality, and the masked image within the map T2 of deteriorating area is visible. The transparency of the mask applied to the map T2 of deteriorating area may be set by the operator.

The edging-line setting unit 69c of the map of deteriorating area processing unit 69 is allowed to function to display the image (see FIG. 8) to obtain the same effect as the one derived from the variable mask value adding unit 69b. The edging-line may be arbitrarily selected by the operator from the solid line, the dashed line and the bold line (required to extend outward). The color of the edging-line may also be freely set by the operator.

The operation console 13 (shown in FIG. 2) may be operated as a scano-imaging executing unit 71 and a scanogram generating unit 72 for generating an image (scanogram) for a positioning of the patient M1.

In a case where the operation console 13 is operated as the scano-imaging executing unit 71 and the scanogram generating unit 72, the map of area outside imaging space generating unit 62 has a function to generate the map of area outside imaging space of the area outside the diameter of the imaging space on the planar sagittal from the area outside the diameter of the imaging space on each planar slice at the rotary axis of the rotary unit 15 as the center based on the diameter of the imaging space (Calib_FOV) and the width of the X-ray detector 24 (DS) in the z-axis direction. In addition, the map of deteriorating area generating unit 63 has a function to generate the map of deteriorating area of the deteriorating area on the planar sagittal from the deteriorating area on each planar slice at the rotary axis of the rotary unit 15 as the center based on the diameter of the imaging space, the width of the X-ray detector 24 in the body axis direction, and the non-deteriorating area generated by the deteriorating area generating unit 61.

Figure 9:
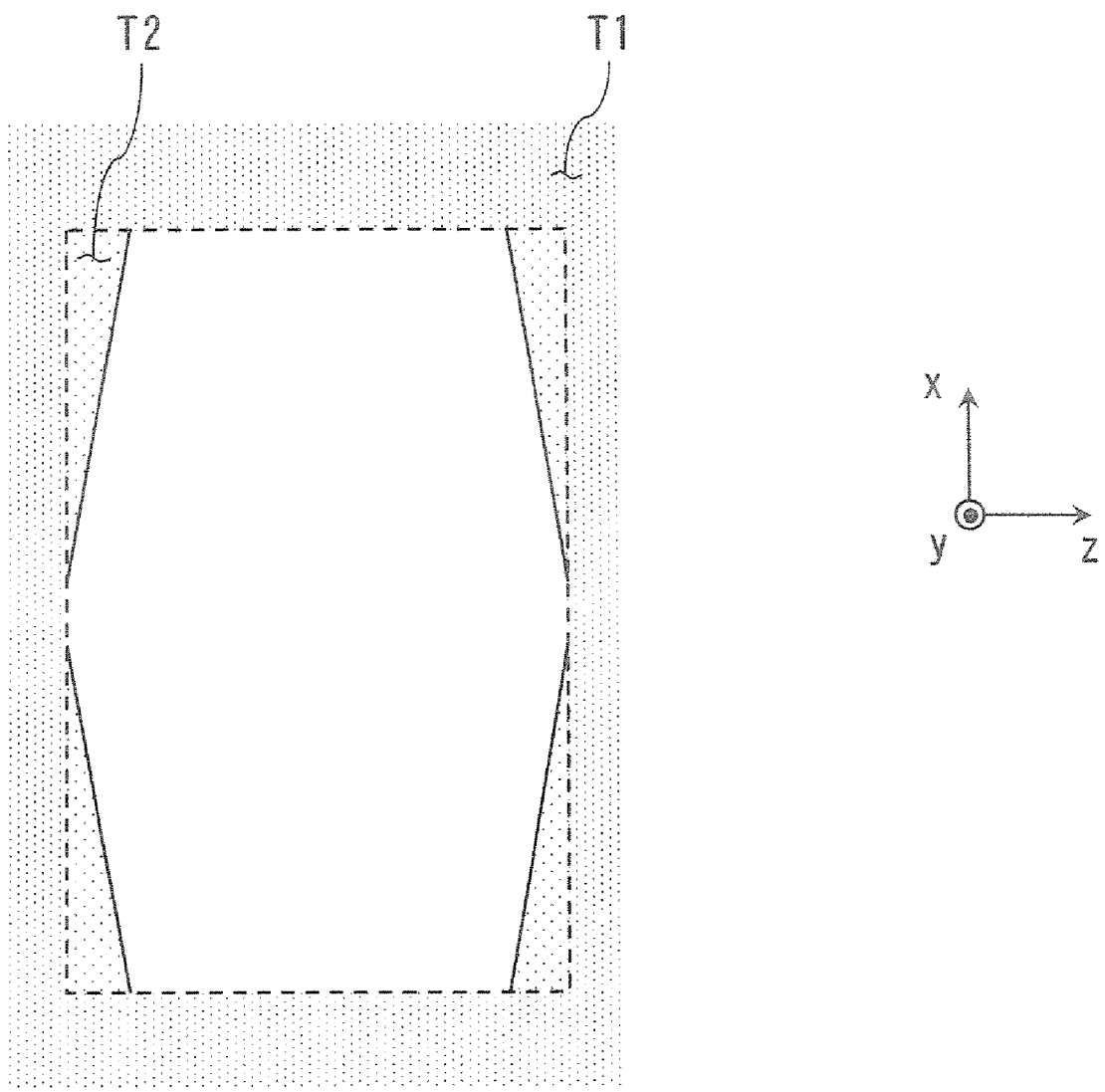
FIG. 9 is a diagram showing an example of the map of area outside imaging space and the map of deteriorating area.

FIG. 9 is a diagram showing an example of the map of area outside imaging space and the map of deteriorating area.

FIG. 9 shows the map T1 of area outside imaging space generated from the outside imaging space area on each planar slice at the rotary axis of the rotary unit 15 (shown in FIG. 1) as the center to appear on the planar sagittal, and the map T2 of deteriorating area generated from the deteriorating area to appear on the planar sagittal. In addition, FIG. 9 shows the map T1 of area outside imaging space and the map T2 of deteriorating area to appear on the scanogram.

When the map T1 of area outside imaging space and the map T2 of deteriorating area are applied on the scanogram, the scanogram and an image of a mark indicating the scan range (dashed line in FIG. 9) may be displayed by superimposing. The map T2 of deteriorating area may be displayed on the scanogram together with the scan range to clarify that the scan range is different from an imaging range (of the data with maintained quality). The image processing unit 67 may be structured to perform at least one of the image processing to hide the display, to change the color and to lower the contrast with respect to the deteriorating area on the scanogram.

The scano-imaging executing unit 71 has a function to execute a scano-imaging. In the scano-imaging, the X-ray irradiation and the data acquisition are performed while keeping the rotation of the rotary unit 15 stopped under the control of the main controller 31. The projection data acquired through the scano-imaging are transmitted to the operation console 13.

The scanogram generating unit 72 has a function to generate the scanogram by arranging the projection data transmitted to the operation console 13 in accordance with the detecting position via the storage device such as the HD 44 in the operation console 13.

The operation console 13 may be operated as a planar reconstructing unit 81.

In the case where the operation console 13 is allowed to function as the planar reconstructing unit 81, the map of area outside imaging space generating unit 62 has a function to generate the map of area outside imaging space of the area outside the diameter of the imaging space appeared on the a planar-MPR (multi planar reconstruction), generated by using an MPR processing, from the area outside the diameter of the imaging space on each planar slice at the center that coincides with reconstruction center based on the diameter of the imaging space (Calib_FOV) and the width of the X-ray detector 24 (DS) in the z-axis direction. The map of deteriorating area generating unit 63 generates the map of deteriorating area of the deteriorating area appeared on the planar-MPR from the deteriorating area generated on each planar slice at the center that coincides with the reconstruction center based on the diameter of the imaging space, the width of the X-ray detector 24 in the body axis direction, and the non-deteriorating area generated by the non-deteriorating area generating unit 61.

The planar reconstructing unit 81 has a function to generate an MPR image by reconstructing the image on the planar-MPR different from the CT image, that is, coronal image, sagittal image and oblique image, based on a plurality of CT images reconstructed by the image reconstruction processing unit 66.

Figure 10:
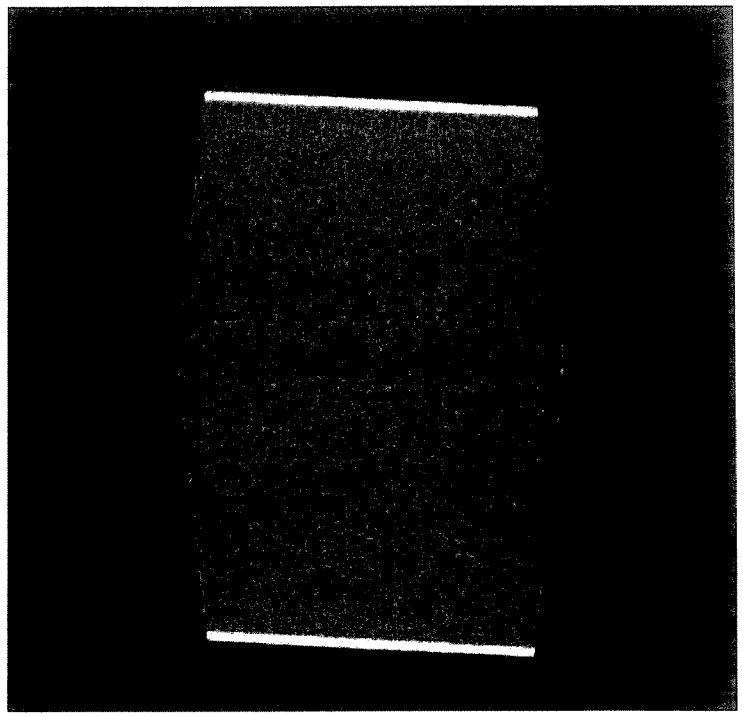
FIG. 10 is a diagram showing an example of display method of the image including an MPR (sagittal) image.
Figure 11:
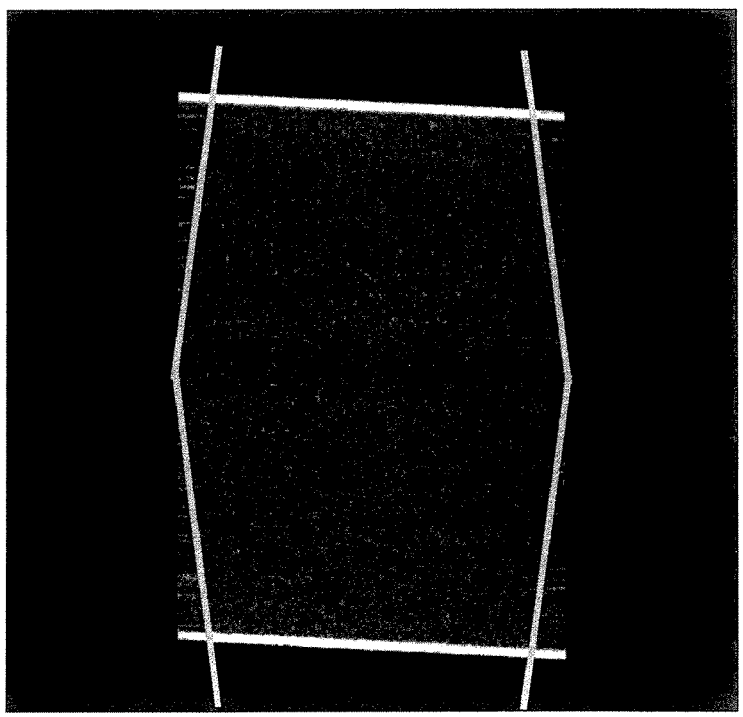
FIG. 11 is a diagram showing an example of display method of the image including the MPR image.

FIGS. 10 and 11 are each diagram showing an example of display method of an image including the MPR (sagittal) image.

Each of FIGS. 10 and 11 shows the MPR image obtained by scanning the cylinder M2 that contains water and performing the planar reconstruction at the sagittal plane. FIG. 10 shows the MPR image superimposed with the map T2 of deteriorating area in which the pixel value is replaced with the mask value by the mask value replacing unit 69a of the map of deteriorating area processing unit 69. Meanwhile, FIG. 11 shows the MPR image in which the edging-line is drawn inside the inner rim of the map T2 of deteriorating area by operating the edging-line setting unit 69c of the map of deteriorating area processing unit 69. FIGS. 10 and 11 show the display images in the case where the rotary axis of the rotary unit 15 coincides with the reconstruction center. However, it is not limited to the one as described above. The rotary axis of the rotary unit 15 does not have to coincide with the reconstruction center.

Figure 12:
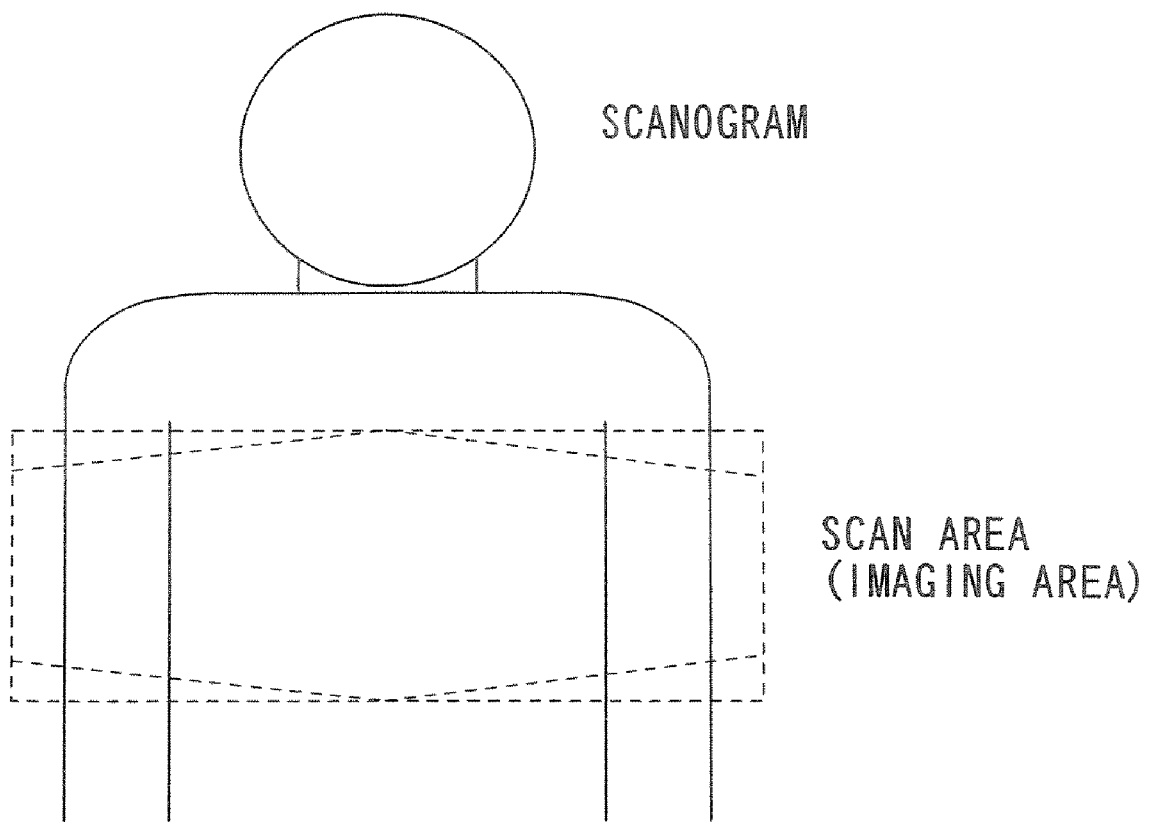
FIG. 12 is a conceptual diagram showing an example of display method of a scanogram.

FIG. 12 is a conceptual diagram showing an example of display method of the scanogram.

FIG. 12 shows a concept of the scanogram in which the edging-line showing a scan area or an imaging area is drawn inside the inner rim of the map T2 of deteriorating area by operating the edging-line setting unit 69c of the map of deteriorating area processing unit 69. In addition, when the scanogram is displayed, it is chosen display of the deteriorating area or non-display of the deteriorating area.

The embodiment of the present invention may be applied to the processing of a three-dimensional image generated based on a plurality of CT images at the corresponding planar slices. The image processing unit 58 obtains a range of the deteriorating areas and the non-deteriorating areas on the CT images at the respective plural planar slices, and performs the image processing for the three-dimensional image obtained based on the CT images so as to discriminate the deteriorating area from the non-deteriorating area.

According to the X-ray CT apparatus 10 of the present embodiment, the image that can effectively perform an inspection and an interpretation of radiogram is offered by generating the image obtained by appropriately changing the display format on the non-deteriorating area.

Figure 13:
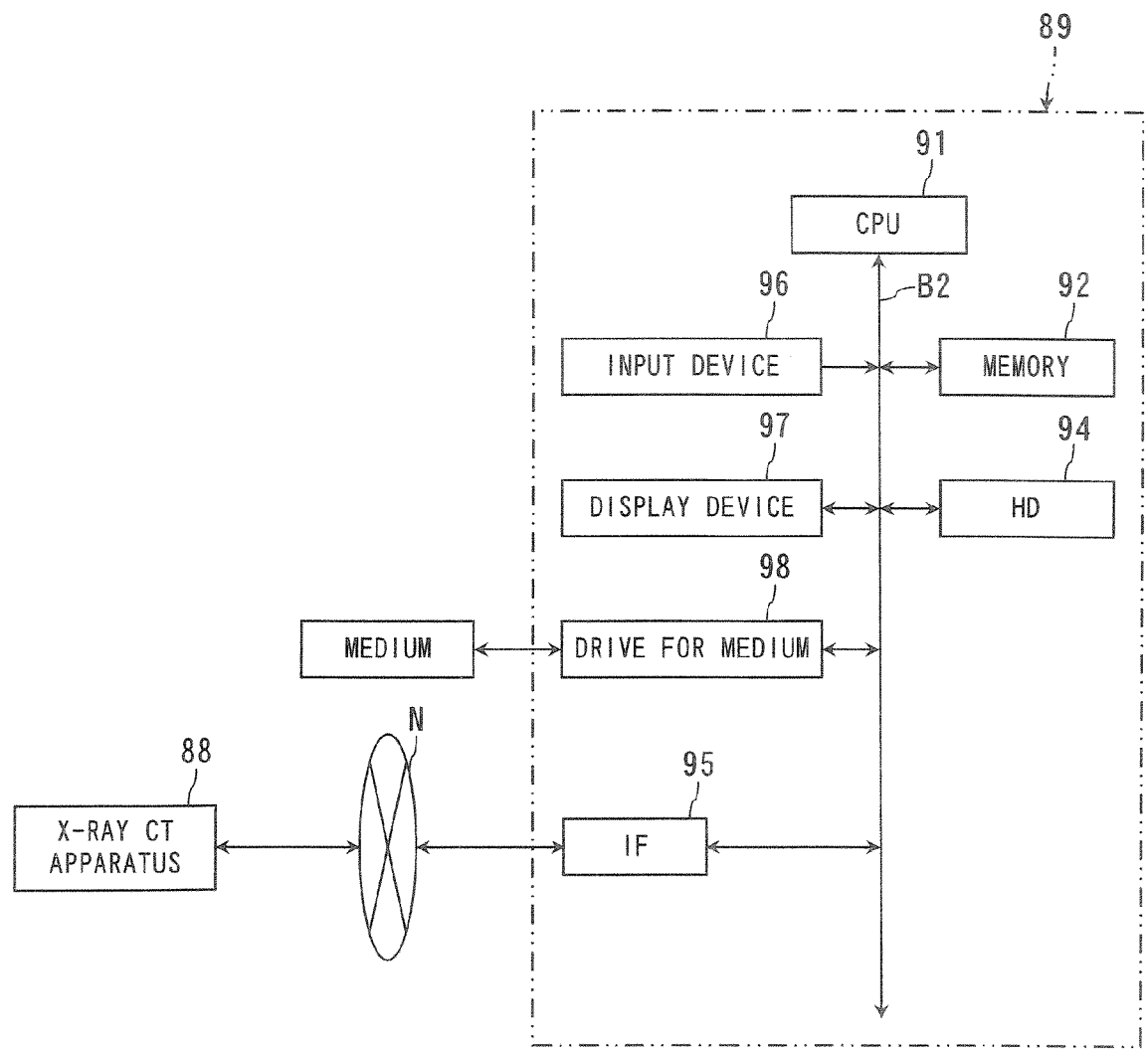
FIG. 13 is a block diagram showing an embodiment of a image display apparatus according to the present invention.

FIG. 13 is a block diagram showing an embodiment of the image display apparatus according to the present invention.

FIG. 13 shows a generally employed X-ray CT apparatus 88 which acquires the projection data while rotating the X-ray source for emitting the X-ray beam and the X-ray detector with multi-arrayed detecting elements along the slice direction around the rotary axis to perform the back projection in consideration with the cone angle of the X-ray beam such that the CT image is reconstructed, and an image display apparatus (viewer) 89 connected to the X-ray CT apparatus 88 so as to be communicated via the network N.

The image display apparatus 89 is formed of a basic hardware including a CPU 91, a memory 92, a HD 94, an IF 95, an input device 96 and a display device 97. The CPU 41 is interconnected with the respective units of the hardware for constituting the image display apparatus 89 via a bus B2 as the common signal transmission path. A drive for medium 98 may be added to the image display apparatus 89. In the embodiment, the image display apparatus 89 is structured to obtain the CT image from the X-ray CT apparatus 88 via the network N. However, it is not limited to the aforementioned structure. It may be structured to record the CT image generated by the X-ray CT apparatus 88 in the recording medium that will be read by the drive for medium 98 of the image display apparatus 89 for obtaining the CT image from the X-ray CT apparatus 88.

As the CPU 91, the memory 92, the HD 94, the IF 95, the input device 96, the display device 97 and the drive for medium 98 have the same functions as those of the respective units as shown in FIG. 1, that is, the CPU 41, the memory 42, the HD 44, the IF 45, the input device 46, the display device 47 and the drive for medium 48, explanations of those components will be omitted.

Figure 14:
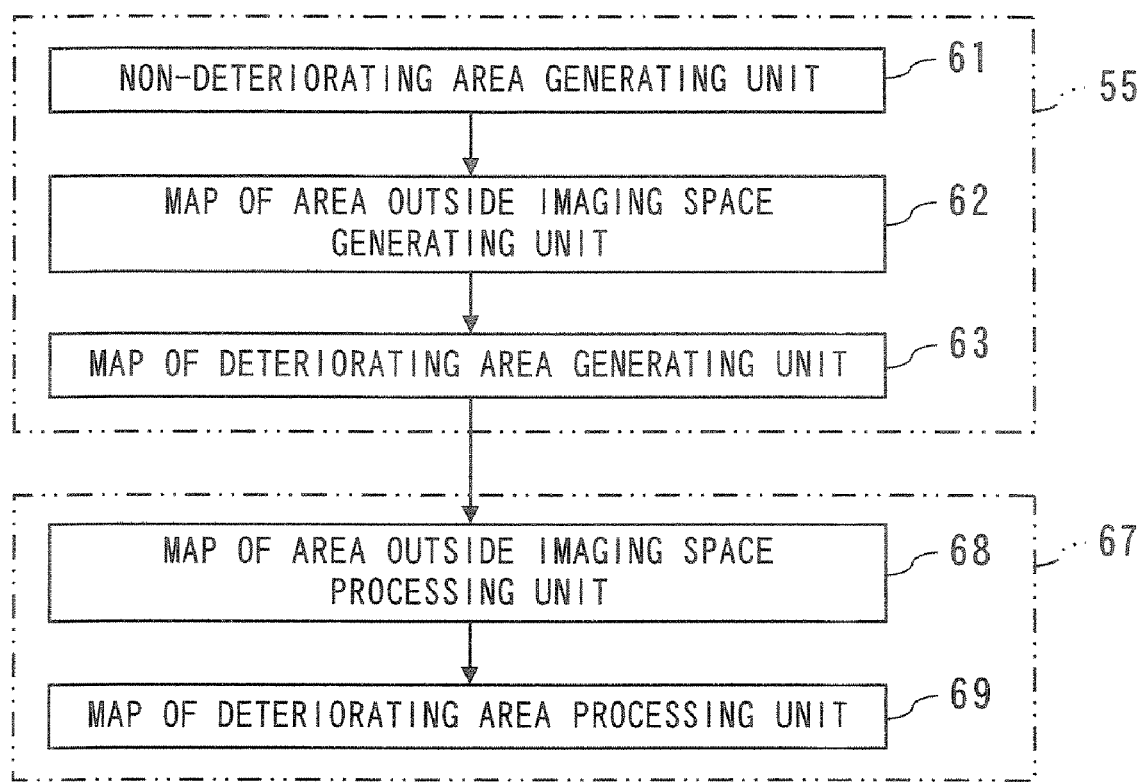
FIG. 14 is a functional block diagram showing the embodiment of the image display apparatus.

FIG. 14 is a functional block diagram showing the image display apparatus 89.

Upon execution of the program by the CPU 91 of the image display apparatus 89 (shown in FIG. 13) the image display apparatus 89 functions as the area arithmetic unit 55 and the display controlling unit 67. In the present embodiment, the respective units 55 and 67 are operated by execution of the program. However, the respective functions of those units may be formed as the hardware of the image display apparatus 89.

As has been described referring to FIG. 2, the area arithmetic unit 55 has the non-deteriorating area generating unit 61, the map of area outside imaging space generating unit 62, and the map of deteriorating area generating unit 63.

The display controlling unit 67 has the map of area outside imaging space processing unit 68 and the map of deteriorating area processing unit 69 as has been described referring to FIG. 2.

The display controlling processing unit 67 of the image display apparatus 89 displays the CT image on the display device 97 such that the deteriorating area is discriminated from the area other than the deteriorating area based on the information with respect to the position of the deteriorating area obtained by the area arithmetic unit 55. The person who interprets the radiogram, for example, doctor is able to interpret while viewing the display image on the display device 97. This makes it possible to the interpreter of the radiogram to perform accurate interpretation with the display image.

The image display apparatus 89 of the present embodiment generates the display image obtained by appropriately changing the display format of the non-deteriorating area with relatively sufficient projection data, based on which the inspection and interpretation of the radiogram are optimally performed.

According to the image display apparatus 89 of the present embodiment, the image that can effectively perform an inspection and an interpretation of radiogram is offered by generating the image obtained by appropriately changing the display format on the non-deteriorating area.

What is claimed is:

1. An X-ray computed tomography apparatus that acquires projection data while rotating an X-ray source for emitting an X-ray beam and an X-ray detector including multi-arrayed detecting elements along a slice direction around a rotary axis, and reconstructs a CT image by performing a back projection in consideration with a cone angle of the X-ray beam, comprising:

an area arithmetic unit configured to generate a non-deteriorating area, appeared on the CT image at each planar slice to assume a center of a rotary axis of the X-ray detector to be a center on the basis of a diameter of an imaging space, a width of the X-ray detector in a z-axis direction, a distance between the X-ray source and the X-ray detector, and a diameter of a non-deteriorating area on a planar slice at a distal end, and obtain information with respect to a position of a deteriorating area near an end of an acquisition range of the projection data under an influence of the cone angle on the basis of the non-deteriorating area;

a map of area outside imaging space generating unit configured to generate a map of an area outside a diameter of the imaging space on a planar sagittal from an area outside the diameter of the imaging space on each planar slice at the rotary axis; and an image processing unit configured to perform an image processing for the CT image so that a first part image of the CT image indicating the deteriorating area and a second part image of the CT image indicating the non-deteriorating area are generated on the basis of the information with respect to the position of the deteriorating area, wherein the deteriorating area is obtained by reconstructing a data area where a first data area of first projection data obtained at a certain projection angle and a second data area of second projection data obtained at an opposed projection angle do not overlap, where there exists the first projection data obtained at the certain projection angle and the second projection data obtained at the opposed projection angle; and the image processing unit performs a variable mask processing of forming a mask by adding a variable mask value to each pixel value in the deteriorating area so that the deteriorating area has a different character on the CT image from the non-deteriorating area, wherein a transparency of the mask in the deteriorating area is variable.

2. The X-ray computed tomography apparatus of claim 1, wherein the image processing unit obtains a range of the deteriorating area and the non-deteriorating area at respective plural CT images, and performs image processing for a three-dimensional image obtained on the basis of the plural CT images that is different for the deteriorating area and the non-deteriorating area.

3. The X-ray computed tomography apparatus of claim 1, further comprising an input device configured to enable a signal input expressing a size of the deteriorating area, wherein the image processing unit obtains the deteriorating area and the non-deteriorating area on the basis of information of the signal input.

4. The X-ray computed tomography apparatus of claim 1, wherein the area arithmetic unit obtains the information with respect to the deteriorating area by comparing the first data area of the first projection data obtained at the certain projection angle and the second data area of the second projection data obtained at the opposed projection angle.

5. An X-ray computed tomography apparatus that acquires projection data while rotating an X-ray source for emitting an X-ray beam and an X-ray detector including multi-arrayed detecting elements along a slice direction around a rotary axis, and reconstructs a CT image by performing a back projection in consideration with a cone angle of the X-ray beam, comprising:

- an area arithmetic unit configured to generate a non-deteriorating area, appeared on the CT image at each planar slice to assume a center of a rotary axis of the X-ray detector to be a center on the basis of a diameter of an imaging space, a width of the X-ray detector in a z-axis direction, a distance between the X-ray source and the X-ray detector, and a diameter of a non-deteriorating area on a planar slice at a distal end, and obtain information with respect to a position of a deteriorating area near an end of an acquisition range of the projection data under an influence of the cone angle on the basis of the non-deteriorating area;
- a map of area outside imaging space generating unit configured to generate a map of an area outside a diameter of the imaging space on a planar sagittal from an area outside the diameter of the imaging space on each planar slice at the rotary axis; and
- an image processing unit configured to perform an image processing for the CT image so that a first part image of the CT image indicating the deteriorating area and a second part image of the CT image indicating non-deteriorating area are generated on the basis of the information with respect to the position of the deteriorating area,
- wherein the deteriorating area is obtained by reconstructing a data area where a first data area of first projection data obtained at a certain projection angle and a second data area of second projection data obtained at an opposed projection angle do not overlap, where there exists the first projection data obtained at the certain projection angle and the second projection data obtained at the opposed projection angle, and the image processing unit performs an operation to lower a contrast of the deteriorating area with respect to the non-deteriorating area.

6. The X-ray computed tomography apparatus of claim 5, wherein the image processing unit obtains a range of the deteriorating area and the non-deteriorating area at respective plural CT images, and performs image processing for a three-dimensional image obtained on the basis of the plural CT images that is different for the deteriorating area and the non-deteriorating area.

7. The X-ray computed tomography apparatus of claim 5, further comprising an input device configured to enable a signal input expressing a size of the deteriorating area, wherein the image processing unit obtains the deteriorating area and the non-deteriorating area on the basis of information of the signal input.

8. The X-ray computed tomography apparatus of claim 5, wherein the area arithmetic unit obtains the information with respect to the deteriorating area by comparing the first data area of the first projection data obtained at the certain projection angle and the second data area of the second projection data obtained at the opposed projection angle.

\* \* \* \* \*